United States Patent
Murray

(10) Patent No.: US 11,587,686 B2
(45) Date of Patent: Feb. 21, 2023

(54) BIOSECURITY SCREENING SYSTEM AND METHOD

(71) Applicant: Cepheid, Sunnyvale, CA (US)

(72) Inventor: William E. Murray, Hilton Head, SC (US)

(73) Assignee: Cepheid, Sunnyvale, CA (US)

(*) Notice: Subject to any disclaimer, the term of this patent is extended or adjusted under 35 U.S.C. 154(b) by 384 days.

(21) Appl. No.: 15/518,735

(22) PCT Filed: Oct. 12, 2015

(86) PCT No.: PCT/US2015/055146
§ 371 (c)(1),
(2) Date: Apr. 12, 2017

(87) PCT Pub. No.: WO2016/089477
PCT Pub. Date: Jun. 9, 2016

(65) Prior Publication Data
US 2017/0308679 A1 Oct. 26, 2017

Related U.S. Application Data

(60) Provisional application No. 62/064,771, filed on Oct. 16, 2014.

(51) Int. Cl.
| | |
|---|---|
| *G16H 50/80* | (2018.01) |
| *G16H 10/40* | (2018.01) |
| *A61B 10/00* | (2006.01) |
| *B01L 3/00* | (2006.01) |
| *C12Q 1/6888* | (2018.01) |
| *C12Q 1/70* | (2006.01) |
| *G01N 33/487* | (2006.01) |
| *G01N 35/02* | (2006.01) |
| *G16H 70/60* | (2018.01) |

(52) U.S. Cl.
CPC ......... *G16H 50/80* (2018.01); *A61B 10/0096* (2013.01); *B01L 3/502* (2013.01); *C12Q 1/6888* (2013.01); *C12Q 1/701* (2013.01); *G01N 33/48792* (2013.01); *G01N 35/021* (2013.01); *G16H 10/40* (2018.01); *G16H 70/60* (2018.01); *B01L 2300/0627* (2013.01); *B01L 2300/087* (2013.01)

(58) Field of Classification Search
CPC .............. G16H 50/80; G01N 35/021; G01N 33/48792; A61B 10/0096; C12Q 1/701; C12Q 1/6888; B01L 3/502; B01L 2300/087; B01L 2300/0627; G06Q 50/22; Y02A 90/24; Y02A 90/22
See application file for complete search history.

(56) References Cited

U.S. PATENT DOCUMENTS

| | | | |
|---|---|---|---|
| 2004/0166550 A1 | 8/2004 | Sullivan et al. | |
| 2007/0229290 A1 | 10/2007 | Kahn et al. | |
| 2009/0221059 A1* | 9/2009 | Williams | B01L 3/0275 435/287.2 |
| 2009/0325276 A1* | 12/2009 | Battrell | B01F 11/0071 435/287.2 |
| 2010/0042394 A1* | 2/2010 | Khan | G06Q 10/04 703/11 |
| 2012/0035279 A1* | 2/2012 | Miller | C12Q 1/68 514/789 |
| 2012/0288897 A1* | 11/2012 | Ching | B01L 3/0265 435/91.2 |
| 2013/0138451 A1* | 5/2013 | Shiono | G06F 19/34 705/2 |
| 2013/0266948 A1* | 10/2013 | Bird | B01F 5/12 435/6.12 |
| 2014/0272928 A1* | 9/2014 | Rey | B01L 3/545 435/5 |
| 2016/0175835 A1* | 6/2016 | Taylor | G01N 1/38 422/522 |

FOREIGN PATENT DOCUMENTS

| | | | | |
|---|---|---|---|---|
| JP | 2009031887 | | 2/2012 | |
| WO | WO-9716561 A1 * | | 5/1997 | ......... B01J 19/0093 |
| WO | 2013/120199 A1 | | 8/2013 | |
| WO | WO-2013173524 A2 * | | 11/2013 | ............... B65B 3/04 |

OTHER PUBLICATIONS

Lorence et al., Computerized Disease Profiling Using GPS-Linked Multi-Function Sensor Cartridges, Jun. 11, 2011, Journal of Medical Systems, pp. 2537-2545. (Year: 2011).*
Gottheil et al., Moving the solid phase: a platform technology for cartridge based sandwich immunoassays, Feb. 2014, Biomedical Microdevices, pp. 163-172. (Year: 2014).*
International Search Report PCT/US2015/055146, dated Mar. 18, 2016.
Johnston, et al. "Fever in returned travellers presenting in the United Kingdom: recommendations for investigation and initial management." Journal of Infection 59, No. 1 (2009): 1-18.
Malone, et al. "US airport entry screening in response to pandemic influenza: modeling and analysis." Travel Medicine and Infectious Disease 7, No. 4 (2009): 181-191.

* cited by examiner

*Primary Examiner* — Christopher L Gilligan
(74) *Attorney, Agent, or Firm* — Kilpatrick Townsend & Stockton LLP

(57) ABSTRACT

The present invention provides systems and methods for rapid screening of individuals who may have been exposed to and carrying biological agents potentially contagious or otherwise harmful to the general public.

30 Claims, No Drawings

BIOSECURITY SCREENING SYSTEM AND METHOD

RELATED PATENT APPLICATIONS

This application is a U.S. National Phase of PCT/US2015/055146, filed Oct. 12, 2015, which claims priority to U.S. Provisional Patent Application No. 62/064,771, filed Oct. 16, 2014, the contents of which are hereby incorporated by reference in the entirety for all purposes.

BACKGROUND OF THE INVENTION

With rapid development in technologies, today's world is becoming an increasingly connected environment. Air travel allows an individual to easily move around the globe from one continent to another within 24 hours. On the other hand, the ease of air travel can also quickly expose the global population to deadly diseases or other harmful effects, leading to potentially devastating results. For example, several years ago the outbreaks of Severe Acute Respiratory Syndrome (SARS) and avian influenza in Asia caused significant concerns in countries on other continents when receiving travelers from the Asian countries affected by the outbreaks. More recently, the epidemic of Ebola hemorrhagic fever in West Africa and the emergence of this disease in the United States have prompted the US government to activate screening procedures at selected airports in an effort to identify and isolate travelers who originated from the Ebola affected nations and exhibit symptoms of Ebola infection. In addition to outbreaks of various infectious diseases, other events, such as acts of terrorism, sabotage, or war where biological or chemical weapons are deployed, also have the potential to very rapidly affect a large population of humans as well as other species due to the highly mobile nature of today's world. As such, there exists a clear need for new and effective means to quickly and accurately identify individuals who have been exposed to and are carrying contagious pathogens or other harmful agents that could be spread into a previously uncontaminated environment.

Screening procedures currently in place for identifying individuals carrying a dangerous biological agent such as a contagious pathogen primarily rely on the detection of symptoms of the disease caused by the biological agent. For instance, the key device for identifying SARS or Ebola carriers at airports is one that can measure individual travelers' body temperature and detect a fever. This type of symptom-based detection methodology is completely ineffective, however, when a carrier of a harmful biological agent is yet to exhibit any clinical symptoms, e.g., due to the incubation period of a viral infection cycle. While others have previously proposed DNA-based detection methods in the context of screening for carriers of potentially transmissible biological agents (see, e.g., JP 2009/031887 and US2012/0035279), to this date there are no established screening systems that can (1) simultaneously perform tests on a large number of individuals, optionally for multiple biological agents, (2) obtain rapid and reliable test results, and (3) permit the authorities to immediately decide whether subsequent movement of the pertinent individuals should be restricted, even before any clinical symptoms become apparent. Considering that these features are important to the effectiveness of a biosecurity screening system and to the ultimate success in protecting the general public from potentially harmful biological agents, development of new methods that can offer these important features is urgently needed. This invention fulfills this and other related needs.

BRIEF SUMMARY OF THE INVENTION

In the first aspect, the present invention provides a biosecurity screening system for rapid identification of individuals carrying a pre-determined biological agent. This biosecurity system includes these components: (a) a passenger information apparatus, which correlates a sample taken from a passenger to a diagnostic test cartridge and to a ticket belonging to the passenger, and which is in communication with (i) a first database containing information of geographic locations and infectious diseases prevalent to the geographic locations, and (ii) a second database containing information of geographic locations in passengers' travel itinerary, wherein the apparatus generates a request for diagnostic testing for a passenger, when an overlap is detected between the geographic locations of the first database and the geographic locations in the passenger's travel itinerary in the second database, for a pathogen or pathogens causing the infectious disease(s) prevalent to the overlapping geographic location(s), and wherein the apparatus generates an alert signal to a ticket reader for the ticket belonging to the passenger, when the diagnostic testing result indicates the presence of the pathogen or pathogens in the sample; (b) at least one diagnostic test cartridge, which (i) comprises a chamber for receiving the sample or an extract thereof, and (ii) contains at least one diagnostic test reagent for detecting the presence of the pathogen or pathogens; (c) at least one diagnostic testing instrument, which performs a diagnostic test on the sample in the at least one diagnostic test cartridge to generate a test result that reports the presence or absence of the pathogen or pathogens in the sample; and (d) a communication means for sending the test result to the passenger information system.

In some embodiments of the claimed system, the sample being analyzed is blood, saliva, sweat, tear, urine, a swab of oral, nasal, or rectal mucosa, or a swab of skin or clothing. In some embodiments, the at least one diagnostic test cartridge comprises a sample chamber to receive the sample or an extract thereof, a reagent chamber for storing the at least one diagnostic test reagent, and a reaction chamber for conducting the diagnostic testing, wherein the sample chamber, the reagent chamber, and the reaction chamber are in selective fluidic communication with each other. In some embodiments, the at least one diagnostic testing instrument does not remove any substance from the at least one diagnostic cartridge. In some embodiments, a plurality of diagnostic cartridges are placed within one diagnostic testing instrument to perform diagnostic testing for a plurality of pathogens. In some embodiments, the diagnostic testing comprises detection of a nucleic acid or a protein.

In some embodiments of the claimed system, the diagnostic testing comprises an amplification reaction of a nucleic acid. The amplification reaction includes a polymerase chain reaction (PCR), such as a real time PCR. In some embodiments, the passenger information apparatus further sends the test result to a mobile device belonging to the passenger. In some embodiments, the first database is updated every 24 hours. In some embodiments, the passengers' travel itinerary comprises all geographic locations the passengers traveled to within the previous 20 days. In some embodiments, the pathogen is the Ebola virus.

In some embodiments of the claimed system, the system further includes a conveyance apparatus for transport of the sample or samples. In some embodiments, the system further includes a conveyance apparatus for transport of the diagnostic test cartridge(s) containing the sample(s) to the diagnostic testing instrument. In some embodiments, the conveyance apparatus is a conveyor belt.

In the second aspect, the present invention provides a method for rapid identification of individuals carrying a pre-determined biological agent. This method is useful for performing biosecurity assessment of passengers and includes these steps: (a) comparing a first database containing information of geographic locations and infectious diseases prevalent to the geographic locations with a second database containing information of geographic locations in passengers' travel itinerary to identify a passenger whose travel itinerary contains geographic locations overlapping with geographic locations in the first database; (b) depositing a sample taken from the passenger identified in step (a) or an extract thereof into at least one diagnostic test cartridge, which (i) comprises a chamber for receiving the sample, and (ii) contains at least one diagnostic test reagent for detecting the presence of a pathogen or pathogens; (c) using at least one diagnostic testing instrument to perform a diagnostic test on the sample in the at least one diagnostic test cartridge to generate a test result that reports the presence or absence in the sample of a pathogen or pathogens causing the infectious disease(s) prevalent to the overlapping geographic location(s); and (d) communicating the test result to a passenger information apparatus, which correlates the sample taken from a passenger to a diagnostic test cartridge and to a ticket belonging to the passenger, and which generates an alert signal to a ticket reader for the ticket belonging to the passenger, when the diagnostic testing result indicates the presence or absence of the pathogen or pathogens in the sample.

In some embodiments of the claimed method, the sample being analyzed is blood, saliva, sweat, tear, a swab of oral or nasal mucosa, or a swab of skin or clothing. In some embodiments, the at least one diagnostic test cartridge comprises a sample chamber to receive the sample, a reagent chamber for storing the at least one diagnostic test reagent, and a reaction chamber for conducting the diagnostic testing, wherein the sample chamber, the reagent chamber, and the reaction chamber are in selective fluidic communication with each other. In some embodiments, the at least one diagnostic testing instrument does not remove any substance from the at least one diagnostic cartridge. In some embodiments, a plurality of diagnostic cartridges are placed within one diagnostic testing instrument to perform diagnostic testing for a plurality of pathogens. In some embodiments, the diagnostic testing comprises detection of a nucleic acid or a protein.

In some embodiments of the claimed method, the method further includes a step of automated conveyance of the diagnostic test cartridge to the diagnostic testing instrument. In some embodiments, the diagnostic testing comprises an amplification reaction of a nucleic acid. One example of the amplification reaction is a polymerase chain reaction (PCR), such as real-time PCR.

In some embodiments of the claimed method, the passenger information apparatus further sends the test result to a mobile device belonging to the passenger. In some embodiments, the first database is updated every 24 hours. In some embodiments, the passengers' travel itinerary comprises all geographic locations the passengers traveled to within the previous 20 days. In some embodiments, the method further includes a step of placing the passenger in isolation when the diagnostic testing result indicates the presence of the pathogen or pathogens in the sample. In some embodiments, the pathogen is the Ebola virus. In some embodiments, once the diagnostic testing is completed, the alert signal is also sent to a passenger's mobile communication device.

DEFINITIONS

In this disclosure the term "passenger" refers to any individual being, human or other species, that appears at a place of gathering with the primary purpose of awaiting to be admitted into a new location. The new location may be a transportation vehicle such as an airplane, train, motor vehicle, watercraft, or spacecraft. Or the new location may be another public place such as a stadium, a park, a museum, a public transportation station (e.g., airport, train station, bus terminal), or a public street.

In this disclosure the term "sample" or "biological sample" includes any bodily fluid or secretion/emission collected from a test subject or "passenger," for example, blood and blood fractions or products (e.g., serum, plasma, platelets, red blood cells, and the like), saliva, sweat, tear, breath, lymphatic fluid, or any sections of tissues such as mucosa swabs taken from the oral cavity/tongue, throat area, nasal passage, vagina, rectal area, or the eyes. Samples further include urine, feces, sputum, semen, or vaginal fluids, as well as all other types of tissue sections that can be obtained using routine biopsy methods from a eukaryotic organism including a mammal, such as a primate especially a human. In addition, a "sample" in some cases also encompasses substances superficially present on the exterior of a passenger and/or his belongings and therefore can be collected by wiping the outer clothing, including footwear and headwear, glasses or goggles, gloves, or skin/hair/fur/features and the like of a passenger who is subject for testing.

In this disclosure a "pathogen" refers to any agent that can cause a disease or condition afflicting human or another species, including animals or plant species. Typically contagious, "pathogens" within the meaning of this application include any disease-causing bacteria, viruses, prions, fungi, or protozoa that can infect their respective hosts, which may be animals (including primates such as human), plants, algae, or other microorganisms. A "pathogen" being tested in the screening method and system of this invention can be present in a cell-free state (e.g., a viral particle outside of a host cell), an integrated state (e.g., a retrovirus integrated into a host genome), or a dormant state (e.g., a spore of a bacterium).

The term "nucleic acid" or "polynucleotide" refers to deoxyribonucleic acids (DNA) or ribonucleic acids (RNA) and polymers thereof in either single- or double-stranded form. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms encompass amino acid chains of any length, including full-length proteins (i.e., antigens), wherein the amino acid residues are linked by covalent peptide bonds.

An "amplification reaction" as used herein refers to a reaction during which a polymerase adds nucleotides to the 3' end of a polynucleotide such that a new strand of polynucleotide is synthesized. Such amplification or extension reactions and the conditions necessary for such reactions are well known in the art, for descriptions, see, e.g., Sambrook and Russell, *Molecular Cloning: A Laboratory Manual,* 3rd Edition, 2001, Cold Spring Harbor Laboratory Press and Ausubel, et al, *Current Protocols in Molecular Biology,* 1987-2007, John Wiley & Sons. The polymerase chain reaction or PCR is a well-known example of an amplification reaction, see, e.g., U.S. Pat. No. 4,683,195; and Saiki et al., (1988) "Primer-directed enzymatic amplification of DNA with a thermostable DNA polymerase" *Science* 239 (4839): 487-491.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, which can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., a segment of the genomic sequence of a pathogen or a cDNA derived therefrom. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site," means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

DETAILED DESCRIPTION OF THE INVENTION

I. Introduction

The present invention provides a biosecurity screening system and a method of using the system for detecting individuals that may be carrying harmful biological agents. In general, the system includes the following components: (1) a passenger information apparatus (which correlates the pertinent travel information, test results of each passenger, and the identity of the passenger, e.g., by a ticket or identity token uniquely assigned to each passenger or lot), (2) one or more diagnostic test cartridge (in which sample undergoes diagnostic testing for the pertinent pathogen or pathogens), (3) one or more diagnostic testing instrument (which provides the testing conditions for the cartridge), and (4) a communication means for sending the test result to the passenger information system. The system can further comprise (5) an automated conveyance apparatus for transport of either the sample or the diagnostic test cartridge(s) to the diagnostic testing instrument.

During operation of the system, passengers' travel information, e.g., the geographic locations, such as the cities and countries they have been during the last days or weeks or months or even years, is first compared with information available through a database containing regularly updated information of biological events (e.g., outbreak of an infectious disease) and their geographic locations. When an overlapping of a passenger's travels with a biological event is found, the passenger is identified as one to be tested for potential presence of a biological agent relevant to the biological event, for example, a pathogen that is known to cause the infectious disease. Depending on the overlapping, one or more samples may be obtained from a passenger. Since the databases, especially considering the first database as a database maintained by a government agency and regularly updated for public health information, the passenger information apparatus is in some cases a cloud-based system. The system can also be programmed to flag any passenger traveling from any geographic location for testing.

Depending on the specific biological agent being tested for, an appropriate sample is then chosen for analysis. For instance, if a virus causing a respiratory disease is being tested for, often a passenger's oral or nasal mucosa is swabbed to produce a sample. For particular pathogens, a rectal swab can also be collected. The sample can also be processed at the collection point to produce an extract which is placed in the test cartridge. For example, an inactivation buffer comprising guanidinium thiocyanate and isopropanol can be added to the swab and incubated for a period of time; a extract of the buffer can then be placed into the diagnostic test cartridge. A diagnostic test cartridge, already containing the necessary diagnostic test reagent(s) within the cartridge is then selected for the diagnostic testing. For example, a set of amplification primers capable of amplifying a nucleic acid unique to the Ebola virus genetic material is present in a diagnostic test cartridge for Ebola.

The diagnostic test cartridge includes at least one chamber that receives the sample. In some cases, the diagnostic testing is performed in the same chamber. In other cases, the cartridge has separate chambers, e.g., a sample chamber for initially receiving and processing the sample and then a reaction chamber for mixing the sample with test reagents in order to conduct the diagnostic testing. These chambers are separate but are selective in fluidic communication with each other.

The diagnostic testing is carried out after one or more diagnostic test cartridges have been loaded with samples and then placed into the diagnostic testing instrument. The diagnostic testing instrument is capable of directing the steps of the relevant diagnostic testing on the sample within the cartridges: for example, the instrument controls cyclic temperature changes of the reaction chamber within the test cartridge following appropriate time intervals in accordance with the pre-determined conditions for amplification of a nucleic acid unique to a pathogen being tested. In some cases, the diagnostic testing instrument comprises a detection means (e.g., an optic reader) that report the test result immediately upon completion of the testing process. The diagnostic testing instrument is typically capable of performing different tests for different pathogens on different samples, in other words, the same instrument is capable of providing testing instructions to a heterogeneous collection of test cartridges at the same time, allowing testing for a plurality of different biological agents simultaneously. Due to the highly automated nature of the testing, individual test results are typically available within 2 hours, or within 1 hour, or within 30 minutes, or even within 20 minutes, depending on the pathogen and sample type.

Once the test result is available to indicate whether or not a biological agent being tested for is present in the test sample, the communication means conveys the result to the passenger information apparatus, which in turn informs the relevant authorities of passenger status in regard to the biological agent in question. For example, the apparatus can send a set of instructions to a passenger ticket reader such that when a ticket corresponding to a passenger whose sample has been tested positive for a pre-determined biological agent the reader sounds a signal of alarm, flagging the passenger holding the ticket. The passenger's subsequent movement may then be restricted or monitored, e.g., the passenger may be quarantined for at least the length of time equivalent to an incubation period in the case of a positive test for an infectious pathogen. If appropriate, the passenger may be placed under the care of a physician to immediately start treatment for the harmful effects of being exposed to and/or infected by the biological agent.

II. Passenger Selection

The present invention aims to provide a system and method that can rapidly identify among a large number of passengers potential carriers of a harmful biological agent, such as an infectious pathogen, and then test the potential carriers to either confirm or eliminate them as actual carriers. Within the meaning of this disclosure, "passengers" are often, but not limited to, human travelers who are in the process of traveling from one geographic location to another, or in preparation of being admitted to a conveyance vehicle such as an airplane, a train, a ship/boat, or a motor vehicle to begin their journey, or in preparation of being released into a public venue from a conveyance vehicle such as an airplane, a train, a ship/boat, or a motor vehicle upon completion of their journey. In some cases, "passengers" are human subjects awaiting to be admitted into a public gathering place such as a sports stadium, a recreational park, a commercial center such as a shopping mall or store, or even a school, a hospital, or a conference hall.

In this disclosure, "passengers" also encompass non-human subjects that are in the process of being transported from one location to another. Non-human subjects include various species of farm animals, pets, plants such as vegetables, fruits, nuts, as well as fungi. Such non-human subjects may, for example, carry pathogens that are potentially dangerous to the humans, animals, or plants in the receiving environment.

For identification purposes when performing the biosecurity screening method, each of the passengers is assigned an identifying token, such as a travel or admission ticket for each human traveler or a registration number for each (lot) of the non-human passengers. Detailed travel information is also required, as a part of the process by which the identification token or ticket is issued, to indicate which geographic location(s) each of the passengers has physically been to within a pre-determined time period just prior to the scheduled travel or admission. Typically, this time period is at least 2 weeks prior to the scheduled travel or admission but not exceeding the longest known incubation period of a suspected pathogen, for example, no more than 21 days in the case of screening for carriers of a virus that has a known incubation period of 1-3 weeks. On the other hand, if a harmful agent being tested for takes the form of spores or has a long incubation period, such time period may need to be lengthened to months or even years, considering spores can routinely survive for a very long period of time under adverse conditions. This travel information is used to compare against a public database, which provides a regularly updated record of what biological agents are prevalent to which geographic location(s), such that passengers can be readily identified as those who were at the geographic location(s) at the approximate time when there was an outbreak of infectious disease or an event involving the use of a biological or chemical weapon, and thus those who should be selected for further screening of the relevant biological agent(s).

Depending on the nature of the event or events relevant to a passenger's travel history, one or more biological agents may be screened for. Such biological agents include but are not limited to viruses and bacteria and the like that can cause infectious diseases, for example: *Acinetobacter baumannii*, *Actinomyces israelii*, *Alphaviruses*, *Bacillus anthracis*, *Bartonella henselae*, *Borrelia*, *Brucella*, *Burkholderia*, *Caliciviridae*, *Chlamydia*, *Chlamydophila pneumoniae*, *Clostridium difficile*, *Corynebacterium diphtheriae*, *Coxiella*, Crimean-Congo hemorrhagic fever (CCHF) virus, cytomegalovirus, Dengue viruses, Ebola virus, Enteroviruses, *Fusobacterium*, Hantavirus, Henipah viruses, human immunodeficiency virus (HIV), hepatitis A, B, C, D, and E viruses, influenza viruses, Junin virus, *Kingella kingae*, Lassa virus, *Listeria monocytogenes*, Marburg virus, Measles virus, Moloney Murine Leukemia Virus (MMuLV), Mumps virus, *Mycobacterium leprae* and *Mycobacterium lepromatosis*, *Mycoplasma pneumoniae*, New World arenaviruses, Orthomyxoviridae, Plasmodium, rhinoviruses and coronaviruses (especially SARS coronavirus), Poliovirus, Rickettsia, Rubella virus, Sabia, *Toxoplasma gondii*, *Trypanosoma brucei*, Varicella zoster virus (VZV), *Vibrio cholerae*, West Nile virus, yellow fever virus, and Yersinia pestis.

III. Passenger Information Apparatus

One component of the biosecurity screening system of this invention is the passenger information apparatus. This is the component that selects the passengers to be tested for potential biological agent(s), correlates the test results with passenger tickets, and ultimately provides directions to the operators of the system as to what actions should be taken to which passengers. In order to effectively perform its intended tasks, the passenger information apparatus typically contains a computer-based operating system, which is set up for communication with the first and second databases. In some cases, the apparatus is locally present (e.g., in the form of a physical presence at or near the location where the passengers are); whereas in other cases, the apparatus is a cloud-based system with a web portal permitting local operators to access remotely. In some cases, the passenger information apparatus is in continuous communication with the first and/or second databases.

To perform the first task of coordinating passenger selection for diagnostic testing, the passenger information apparatus is provided with a core computer system containing the appropriate software and/or hardware to receive information originated from two separate databases and then carry out comparison of the relevant information: the first database is a public "bio-alert" database typically maintained and regularly updated by a government agency or international organization such as the Center for Disease Control (CDC) or the World Health Organization (WHO). This database reports the presence of potentially harmful biological agents at any geographic locations world-wide due to infectious disease outbreaks or human actions. The database is updated at least once a week or twice a week, and in some cases at least once a day or even more frequently when appropriate.

The passenger information apparatus is also in communication with a second database, which is a one that contains passenger travel information and is typically maintained by a private or local entity such as a transportation provider (e.g., an airline) or an organizer of an event to which passengers seek to be admitted (e.g., owner of a sports stadium). Information pertaining to a passenger's travel itinerary is typically obtained and entered at the time passenger identification tokens are assigned to individual passengers (e.g., when passenger tickets are purchased). In some cases, the passenger information includes the geographic locations a passenger plans to visit in the immediate future, for example, within the next day, the next 2, 3, 4, 5, 6, or 6 days, or the next week or 2 weeks, or the next month or next 2 months.

Given the distinct nature of the two databases, the first database is typically accessible by the core computer of the passenger information apparatus through web connection only, whereas the second database is in some cases maintained locally and may have a nearby physical presence, e.g., maintained in a computer terminal near the location where the passengers gather and may be directly connected or even contained within the core computer; or in some other cases the second database is accessible remotely only, also via web connection.

Upon receiving the passenger travel information, e.g., which geographic locations they have been to in the pre-determined time period immediately prior to the present time, and receiving the "bio-alert" information from the first database, the passenger information apparatus automatically compares the information and identifies passengers who were present at any geographic locations where a biological event took place within the time frame, especially those who were present at the time of the event or immediately thereafter. The passengers identified by the apparatus following the information comparison as potential carriers of the biological agent(s) relevant to the biological event(s), and appropriate samples are then taken from them depending on the nature of the biological agent to be tested for. For example, when one is tested for the presence of a contagious pathogen affecting the upper respiratory system such as the Ebola virus, often a swab of mucosa from the mouth, nose, or throat area is taken for analysis. On the other hand, when one is tested for the presence of spores of a potentially deadly bacterium such as the anthrax-causing *Bacillus anthracis* after exposure in an act of bio-terrorism, the outer clothing or exposed skin/hair may be wiped for sampling.

The passenger information apparatus is further programmed to receive test results via a communication means from one or more diagnostic testing instrument after diagnostic testing is completed on samples taken from passengers. Typically, the information is automatically transmitted and positive and negative test results are correlated with individual passengers or lots for the specific biological agent(s) tested for via their identity tokens, e.g., passenger tickets. The passenger information apparatus then generates a set of instructions to be transmitted to a reader or scanner of the passenger identity tokens, a device that may be physically connected to the passenger information apparatus or may be wirelessly connected to the passenger information apparatus. The instructions from the passenger information apparatus then direct the reader or scanner to produce an alarm signal once it reads or scans a token corresponding to a passenger whose sample has been tested positive for a biological agent. The alarm signal may be an audible warning or it may be a visual warning. In some cases, the warning specifically indicates the biological agent detected in a passenger sample. In addition, the passenger information apparatus optionally can be set up to convey the test results to passengers' mobile communications device, e.g., a cellular phone, especially a smart phone, a personal computer, a tablet, and the like.

As a further option, the passenger information apparatus can provide warning to passengers who are scheduled to visit geographic locations where a recent event took place involving the spread of certain harmful biological agent(s).

IV. Diagnostic Test Cartridge

Once a passenger is identified as a potential carrier of a harmful biological agent, for example, due to his stay at a geographic location during an outbreak of infectious disease at that location, at least one sample of the appropriate type(s) is then taken from the passenger for diagnostic testing to either confirm or eliminate him as a true carrier of the biological agent. The sample is deposited into a diagnostic testing cartridge for analysis. Depositing samples into the diagnostic test cartridges can be done at or near the point of sample collection or at or near the diagnostic testing instrument location. For example, an automated conveyance method and apparatus, such as a conveyor belt, can be used to transport the diagnostic test cartridges to the diagnostic testing instrument.

A. General Structure

Each diagnostic test cartridge contains pre-selected reagent or reagents specific for testing at least one biological agent. For example, a cartridge intended for detecting a nucleic acid derived from the Ebola virus is labeled "Ebola," such that a sample from a passenger suspected of carrying the Ebola virus may be placed in this cartridge for testing.

In general, a diagnostic test cartridge used in the biosecurity screening system of this invention contains at least one chamber and usually multiple chambers. In the simplest embodiment, the diagnostic test cartridge comprises a chamber that receives the sample and also pre-stores all necessary ingredients for the testing reaction. Once the sample is deposited in the receiving chamber, it can be directly used in the testing reaction. In this situation, the sample chamber that receives the sample also serves as the reaction chamber.

In other cases, the sample in the receiving chamber (i.e., the sample chamber) must be first processed to properly release the analyte and/or remove cell/virus/tissue debris before commencing the diagnostic testing step. As such, the diagnostic test cartridge will have at least one compartment, the sample chamber, which receives the sample and then allows the diagnostic testing to take place. Typically, however, the diagnostic test cartridge used in the biosecurity screening system comprises multiple compartments such as at least one sample chamber where the passenger sample is initially deposited, at least one storage chamber where at least one reaction reagent is stored, often in a dried or lyophilized form, such as reagent beads or powder, until it is ready to be mixed with the test sample and reconstituted into a viable reaction mixture to commence the diagnostic testing reaction. In some cases, all necessary components of a testing reaction are stored in the same storage chamber, whereas in other cases certain ingredients are stored separately from each other in multiple storage chambers.

While it is possible to mix a processed sample with pre-mixed reaction ingredients in a storage chamber to prepare a reaction mixture for conducting the testing reaction (which makes the storage chamber also a reaction chamber), it is most often that a separate chamber is used for mixing all necessary ingredients of a reaction with a processed sample to produce a reaction mixture, which then undergoes a pre-designated biological testing process for identifying a biological agent that a passenger is suspected of carrying. This chamber is thus referred to as the reaction chamber. For the ease of conducting the diagnostic testing, the reaction chamber may be protruding from the main body of the diagnostic test cartridge, as this design permits easy and accessible temperature control of the reaction chamber as well as ready monitoring of reaction progress by the diagnostic testing instrument. In some cases, the reaction chamber comprises at least two transparent walls so as to allow optical interrogation of the reaction mixture during thermal cycling to determine the progress and results of the reaction. Optionally, there is also at least one waste chamber.

In a typical diagnostic test cartridge, aside from multiple chambers, e.g., for receiving and processing the sample, for storing reagents, and for conducting test reaction, there is a fluid control mechanism that directs the movement of fluid from one chamber to another during the course of sample preparation, assembly of reaction mixture, and performance of diagnostic reaction. In some cases, the fluid control mechanism comprises an elongated shaft having a hollow cavity and external ports, and is often located centrally in relation to the locations of the plurality of chambers. The fluid control mechanism is adjustable, often in the rotational motion, so that the external ports can be placed in selective fluid communication with one or more ports of the chambers in the diagnostic test cartridge. The fluid control mechanism contains a means (e.g., a movable piston within the inside space or an air pump) that allows the internal volume of the hollow cavity in the elongated shaft to become pressurized or depressurized such that when it is adjusted to a certain position and becomes connected with the selected one or more of the chambers, fluid can be moved to or from or among the various chambers in the diagnostic test cartridge. This allows the fluid control mechanism to direct all necessary steps of sample processing, assembly of reaction mixture, and disposal of reaction mixture upon completion of the reaction, etc., often in an automated fashion such as instructed by the diagnostic testing instrument following a set of pre-programmed commands.

To ensure accuracy of the test results and to eliminate the risk of contamination, the diagnostic test cartridges used in the present invention are typically closed once the test sample is deposited within the chamber receiving the sample (e.g., the sample chamber). An exemplary design involves a top cap for the cartridge, which can comprise a base portion that is secured onto the top of the cartridge, and a lid portion that can be opened via a hinged connection to the base portion so as to allow addition of the sample to the cartridge and closed. In some cases, the lid portion is secured to the base portion via a snap-fit connection. The movement of fluid among the various chambers is controlled by the fluid control mechanism, which is in turn directed by the diagnostic testing instrument. Typically, all substance within the test cartridge is kept within the cartridge during and after the diagnostic testing is performed.

Various devices may serve as diagnostic test cartridges for use in the biosecurity screening system of this invention. Exemplary diagnostic test cartridges and their uses are described in, e.g., U.S. Pat. Nos. 6,374,684; 6,783,736; 6,818,185; 8,048,386; 8,431,413; 8,673,238; 8,168,442; and 8,709,363. In particular, U.S. Pat. Nos. 5,958,349; 6,565,815; 6,660,228; 7,462,323; and 8,303,895, as well as PCT patent application published as WO2014/052671, describe devices and methods suitable for performing diagnostic testing involving a thermo-cycling amplification reaction (e.g., PCR). U.S. Provisional Patent Application No. 62/196,845, filed on Jul. 24, 2015, further describes advanced systems, devices, and methods for rapidly performing diagnostic assays for the detection of various analytes with the capability of remotely communicating information, such as diagnostic results, with a recipient at a distant location.

In some cases, pre-reaction sample processing is necessary, for example, when cells or viruses need to be adequately disrupted in order for analytes (nucleic acids, proteins, and the like) to be released and/or lysis debris removed in order to achieve accurate diagnostic testing. Devices and methods useful for such purposes may be found in, e.g., U.S. Pat. Nos. 6,391,541; 6,440,725; 6,431,476; 6,881,541; 6,987,018; and 8,268,603. In some cases, the diagnostic testing results generate colorimetric or fluorescent signals and are therefore monitored and quantitatively reported by way of optical interrogation, see, e.g., U.S. Pat. Nos. 6,369,893; 6,565,815; 6,940,598; 8,029,733; and 8,293,064, for description of suitable devices, methods for optic interrogation of reaction, and methods for making such devices.

Diagnostic Assays

As biological agents of different nature are tested for depending on the circumstances, assays of different format may be employed in the diagnostic test cartridges. For instance, when a protein (including an antibody) is being tested for, an immunoassay may be appropriate for identification of the protein based on a known antigen-antibody binding specificity. For example, standard immunological techniques can be used to detect a given protein using the appropriate antibodies. Both monoclonal and polyclonal antibodies (including antibody fragment with desired binding specificity) can be used for specific detection of the protein. In the alternative, a sandwich assay can be performed by capturing the protein of interest from a test sample with an antibody having specific binding affinity for the protein. The protein then can be detected with a labeled antibody having specific binding affinity for it. Non-specific binding is reduced or eliminated by appropriate washing, and detection of the presence of a target protein is facilitated by the use of a detectable label such as a fluorescent label.

In other cases, a polynucleotide sequence derived from a biological agent, e.g., a bacterium or a virus, may be tested for in order to determine the presence or absence of the biological agent in a passenger sample. To ensure detection of a target polynucleotide sequence that might be present at a low concentration in a passenger sample, the diagnostic assays typically involve as a first step an amplification reaction. Optionally the amplification is followed by a detection step involving a sequence-specific hybridization scheme.

Polynucleotide Amplification Reactions

Amplification of an RNA or DNA template using reactions is well known (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of target DNA sequences directly from mRNA, from cDNA, from genomic libraries or cDNA libraries. The reaction is preferably carried out in a thermal cycler to facilitate incubation times at desired temperatures. See, e.g., PCR PRIMER, A LABORATORY MANUAL (Dieffenbach, ed. 2003) Cold Spring Harbor Press. In the instant case, the temperature control for a reaction chamber within the diagnostic test cartridge for a pre-determined length of time is carried out by the diagnostic testing instrument.

Typical PCR reaction conditions allowing for amplification of a target polynucleotide sequence comprise multiple 2- or 3-step cycles. The 2-step cycles have a denaturation step followed by a hybridization/elongation step, whereas the 3-step cycles comprise a denaturation step followed by a hybridization step followed by a separate elongation step. In most cases, a total of 30 to 40 cycles are necessary for a target polynucleotide sequence to be amplified to a level that permits ready detection.

Depending on the nature of the target polynucleotide sequence, a PCR or reverse transcription (RT) PCR may be used as the appropriate amplification reaction: DNA sequences can be directly amplified in a PCR, whereas RNA sequences require RT-PCR for amplification. In some embodiments, an amplified target sequence is detected by real-time PCR. Real-time PCR is a method that utilizes specifically engineered DNA sequences (two primers and a fluorescently labeled probe) to detect and quantify target sequences of DNA. The probe contains a fluorescent reporter dye on one end and a quencher dye on the other. During each amplification cycle, the probe first attaches to the target DNA sequence, followed by attachment of the primers. As the DNA strand is copied, the reporter dye is released from the probe and emits a fluorescent signal. The amount of fluorescence increases with each cycle of PCR in proportion to the amount of target DNA being amplified and accumulated. This results in direct detection and quantification of the target DNA sequence with a high degree of specificity, accuracy, and sensitivity.

In other embodiments, fluorescent dyes preferentially bound to double-stranded (ds) DNA may be used to indicate the progress and completion of a real-time PCR. For instance, SYBR® Green is an asymmetrical cyanine dye frequently used as an agent for staining nucleic acids in molecular biology. Since SYBR® Green preferentially binds to ds DNA, and the resulting DNA-dye-complex absorbs blue light of 497 nm and emits green light of 520 nm, it allows easy and instantaneous detection of presence of target polynucleotide sequences in real-time PCR.

Detection of Amplified Target Polynucleotides

Amplified nucleic acid sequences or amplicons can be detected using any method known in the biomedical research field including those mentioned above. For example, amplicons can be detected using probes that specifically hybridize to the amplicon (i.e., complements to the amplicon sequence) and become detectable (e.g., emitting fluorescence) upon hybridization to the amplicon. A variety of probes are capable of hybridizing to and allowing specific detection of a particular polynucleotide sequence. In some cases, the probe also comprises a fluorophore or enzyme, as described below, which allows for the detection of the binding of the probe to its complementary target sequence.

Probe concentration should be sufficient to bind to the amount of target sequence upon amplification so as to provide an accurate assessment of the quantity of amplicons. Those of skill in the art will recognize that the amount of concentration of probe will vary according to the binding affinity of the probe as well as the quantity of amplicon sequence to be bound. Typical probe concentrations will range from 0.01 µM to 0.5 µM. Typical probe length will range from about 20-40 nucleotide bases in length, for example, about 25-35 nucleotide bases in length, or any integer number of nucleotide bases within these ranges.

The present invention can employ different types of nucleic acid hybridization probes for detection of amplicons. Typically, for signal generation, the probes utilize a change in the fluorescence of a fluorophore due to a change in its interaction with another molecule or moiety brought about by changing the distance between the fluorophore and the interacting molecule or moiety.

In some instances, multiple fluorescent labels are employed. In a preferred embodiment, a Molecular Beacon probe is used, which involves two fluorescent labels, a fluorescence resonance energy transfer (FRET) pair, see Tyagi and Kramer, *Nature Biotechnology* 14: 303-308 (1996). FRET is phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor usually overlap, and the two molecules must be in close proximity for donor's fluorescence emission to be quenched by the acceptor. The distance between donor and acceptor at which 50% of donors are deactivated (transfer energy to the acceptor) is defined by the Forster radius ($R_o$), which is typically 10-100 Å. A molecular beacon probe is a polynucleotide with end regions hybridizing with one another to form a hairpin in the absence of a target (i.e., complementary) polynucleotide sequence, but the ends are separated if the central portion of the probe hybridizes to its target sequence. When the probe hybridizes to a target sequence based on nucleotide sequence complementarity, a relatively rigid helix is formed, causing the stem hybrid to unwind and forcing the ends apart. As such, an increase in the fluorescence emission from the FRET donor indicates hybridization of the probe to a complementary target sequence, thus permitting detection of the target sequence and determining its quantity.

FRET pairs (donor/acceptor) useful in the invention include, but are not limited to, EDANS/fluorescein, IAEDANS/fluorescein, fluorescein/tetramethylrhodamine, fluorescein/LC Red 640, fluorescein/Cy 5, fluorescein/Cy 5.5, fluorescein/LC Red 705, EDANS/DABCYL, Texas Red/DABCYL, BODIPY/DABCYL, Lucifer yellow/DABCYL, coumarin/DABCYL, and fluorescein/QSY 7 dye. In some embodiments, the amplified nucleic acid sequence is detected using a probe labeled at its 5'-end with a fluorophore and at its 3'-end with a quencher. In a further embodiment, the fluorophore is fluorescein (FAM) and the quencher is QSY7. Alternatively, fluorophore(s) and/or quencher(s) can be located at an internal site within a probe.

Another type of nucleic acid hybridization probe assay utilizing a FRET pair is the "TaqMan®" assay described in Gelfand et al. U.S. Pat. No. 5,210,015, and Livak et al. U.S. Pat. No. 5,538,848. The probe is a single-stranded polynucleotide labeled with a FRET pair. In a TaqMan® assay, a DNA polymerase releases single or multiple nucleotides by cleavage of the polynucleotide probe when it is hybridized to a target strand. That release provides a way to separate the quencher label and the fluorophore label of the FRET pair.

Non-FRET fluorescent probes can also be used. For example, changes in the absorption spectra of the label pair can be used as a detectable signal as an alternative to change in fluorescence. When change in absorption is utilized, the label pair may include any two chromophores, that is, fluorophores, quenchers and other chromophores. The label pair may even be identical chromophores.

V. Diagnostic Testing Instrument

Once a test sample obtained from a passenger is deposited into a receiving chamber (e.g. sample chamber) of the diagnostic test cartridge, the cartridge lid is secured before being placed into a diagnostic testing instrument for conducting the appropriate diagnostic testing. In general, a diagnostic testing instrument is a multi-unit instrument that can accommodate multiple test cartridges at the same time and can automatically carry out the necessary steps for performing the corresponding test for each cartridge. An exemplary diagnostic testing instrument may have 2, 4, 5, 8 or more, modules for test cartridges, wherein each module can process a single test cartridge at a time. In some cases, the diagnostic testing instrument contains 16, 48, 80, 100 or more modules for test cartridges. Once a diagnostic test cartridge is placed inside a test module of the diagnostic testing instrument, the instrument is programmed to perform the testing procedures on the individual test cartridge within an individual module independent of other cartridges or modules. For example, a diagnostic testing instrument running 32 sample tests at the same time may be handling 10 samples being tested for Ebola, 10 other samples being tested for Lassa virus, and 12 other samples being tested for Marburg virus. Furthermore, the testing of individual cartridges within separate modules can be performed with different start times. For example, in the illustration described above for an instrument containing 32 modules, the test cartridges could all be started at different times relative to each other. Description for such instrument can be found in, e.g., U.S. Provisional Patent Application No. 61/639,820 and International Patent Application WO2013/163424. A preferred diagnostic testing instrument is the GeneXpert® Infinity 80 System available commercially from Cepheid (Sunnyvale, Calif.), which is capable of processing simultaneously 80 separate diagnostic test cartridges. The GeneXpert® Infinity 80 System also includes an automated conveyor belt for transport of the diagnostic test cartridges for loading into the instrument.

As discussed above, the diagnostic testing instrument directs each and every step of diagnostic testing, including sample preparation, assembly of the reaction mixture, and conducting the reaction. The diagnostic testing instrument contains a set of pre-determined of commands in controlling the movement of fluid within the diagnostic test cartridge among various chambers, e.g., sample chamber, reagent chamber(s), reaction chamber, and optionally waste chamber by way of controlling the actions of the control chamber in an automated fashion. The instrument can then be programmed to carry out different sets of commands for individual test cartridges, depending on the specific biological agent each cartridge is intended to test for.

In some cases, the diagnostic testing procedure involves an amplification reaction such as PCR for detection of signature DNA sequences derived from certain pathogens. For the purpose of efficiently control the temperature of the reaction chamber, the cartridge is designed to make the reaction chamber take the shape of a flat, thin piece protruding from the main body of the cartridge such that when the cartridge is placed in the diagnostic testing instrument the reaction chamber is received between two heating plates that tightly fit the against both sides of the reaction chamber. This design permits instantaneous heating and cooling, thus enhancing the PCR performance.

Since one advantageous feature of the biosecurity screening system of the present invention is rapid testing and rapid results, optic interrogation is often chosen as the means for monitor the test progress and ascertaining the test outcome. As such, the diagnostic testing instrument often contains an optic reader as well as a light emission source. For example, for monitoring the progress of a real-time PCR in which a molecular beacon probe is included, a light emission source will emit an excitation light in appropriate wavelength for the fluorophore, while at the same time the optic reader will be set at the wavelength of the emission from the fluorophore. Typically, a pre-determined value is chosen for each type of test cartridge (i.e., for testing one particular pathogen) to indicate a positive test result.

VI. Communication Means

Once the diagnostic testing is completed, the test results are then forwarded to the passenger information apparatus via a communication means. This communication means in some cases is a direct and physical connection, i.e., an electrical conductor such as a cable or a wire, between the diagnostic test instrument and the passenger information apparatus; in other cases, the communication means is a wireless connection.

VII. Further Steps

Upon detection of the presence of a biological agent in a passenger's sample, immediate actions are taken to first notify the relevant authorities such that necessary quarantine, monitoring, and/or medical treatment of the affected passenger may start as soon as possible. Also, the detection of any harmful biological agent may be reported to a database maintained by a government agency or international health organization such as the CDC and WHO for information purposes. This can be readily achieved by the passenger information apparatus, which is already in communication with such databases on a regular basis. Lastly, the passenger is notified of the results of the diagnostic testing, especially when he or she has been tested positive for certain harmful pathogens, such that appropriate actions may be taken to isolate, monitor, and/or treat the individuals who may have had close contact with the passenger in recent time.

All patents, patent applications, and other publications, including GenBank Accession Numbers, cited in this application are incorporated by reference in the entirety for all purposes.

What is claimed is:

1. A biosecurity system comprising:
(a) a passenger information apparatus, which correlates a sample taken from a passenger to each of a plurality of diagnostic test cartridges and to a ticket belonging to the passenger, and which is in communication with (i) a first database containing information of geographic locations and infectious diseases prevalent to the geographic locations, and (ii) a second database containing information of geographic locations in passengers' travel itinerary, wherein the apparatus generates a request for diagnostic testing for a passenger, when an overlap is detected between the geographic locations of the first database and the geographic locations in the passenger's travel itinerary in the second database, for a pathogen or pathogens causing the infectious disease(s) prevalent to the overlapping geographic location(s), and wherein the apparatus generates an alert signal to a ticket reader for the ticket belonging to the passenger, when the diagnostic testing result indicates the presence of the pathogen or pathogens in the sample;
(b) the plurality of the diagnostic test cartridges, each of which (i) comprises a sample chamber for receiving the sample or an extract thereof, and (ii) comprises a reaction chamber containing at least one diagnostic test reagent for detecting the presence of the pathogen or pathogens, wherein the sample chamber and the reaction chamber are controlled by a pressurizable/depressurizable fluid control mechanism to be selectively in fluidic communication with each other via external ports, and wherein the fluid control mechanism is adjustable in a rotational motion to selectively place the sample chamber and the reaction chamber in fluidic communication with each other;
(c) a diagnostic testing instrument, which contains the plurality of the diagnostic test cartridges and performs a different diagnostic test on the sample in each of the plurality of the diagnostic test cartridges to generate a test result that reports the presence or absence of the pathogen or pathogens in the sample; and
(d) a communication means for sending the test result to the passenger information apparatus.

2. The system of claim 1, wherein the sample is blood, saliva, sweat, tear, urine, a swab of oral, nasal, or rectal mucosa, or a swab of skin or clothing.

3. The system of claim 1, wherein each of the plurality of the diagnostic test cartridges comprises a sample chamber to receive the sample or an extract thereof, a reagent chamber for storing the at least one diagnostic test reagent, and a reaction chamber for conducting the diagnostic testing, wherein the sample chamber, the reagent chamber, and the reaction chamber are in selective fluidic communication with each other.

4. The system of claim 1, wherein the diagnostic testing instrument does not remove any substance from the plurality of the diagnostic test cartridges.

5. The system of claim 1, wherein the diagnostic testing comprises detection of a nucleic acid or a protein.

6. The system of claim 1, wherein the diagnostic testing comprises an amplification reaction of a nucleic acid.

7. The system of claim 6, wherein the amplification reaction is a polymerase chain reaction (PCR).

8. The system of claim 6, wherein the amplification reaction is a real time PCR.

9. The system of claim 1, wherein the passenger information apparatus further sends the test result to a mobile device belonging to the passenger.

10. The system of claim 1, wherein the first database is updated every 24 hours.

11. The system of claim 1, wherein the passengers' travel itinerary comprises all geographic locations the passengers traveled to within the previous 20 days.

12. The system of claim 1, wherein the pathogen is the Ebola virus.

13. The system of claim 1, further comprising a conveyance apparatus for transport of the sample.

14. The system of claim 1, further comprising a conveyance apparatus for transport of the diagnostic test cartridge containing the sample to the diagnostic testing instrument.

15. The system of claim 14, wherein the conveyance apparatus is a conveyor belt.

16. A method of performing biosecurity assessment of passengers, comprising:
(a) comparing a first database containing information of geographic locations and infectious diseases prevalent to the geographic locations with a second database containing information of geographic locations in passengers' travel itinerary to identify a passenger whose travel itinerary contains geographic locations overlapping with geographic locations in the first database;
(b) depositing a sample taken from the passenger identified in step (a) or an extract thereof into a plurality of diagnostic test cartridges, each of which (i) comprises a sample chamber for receiving the sample, and (ii) comprises a reaction chamber containing at least one diagnostic test reagent for detecting the presence of a pathogen or pathogens, wherein the sample chamber and the reaction chamber are controlled by a pressurizable/depressurizable fluid control mechanism to be selectively in fluidic communication with each other via external ports, and wherein the fluid control mechanism is adjustable in a rotational motion to selectively place the sample chamber and the reaction chamber in fluidic communication with each other;
(c) using one diagnostic testing instrument, which contains the plurality of diagnostic test cartridges to perform a different diagnostic test on the sample in each of the plurality of diagnostic test cartridges to generate a test result that reports the presence or absence in the sample of a pathogen or pathogens causing the infectious disease(s) prevalent to the overlapping geographic location(s);
(d) communicating the test result to a passenger information apparatus, which correlates the sample taken from a passenger to a diagnostic test cartridge and to a ticket belonging to the passenger, and which generates an alert signal to a ticket reader for the ticket belonging to the passenger, when the diagnostic testing result indicates the presence or absence of the pathogen or pathogens in the sample.

17. The method of claim 16, wherein the sample is blood, saliva, sweat, tear, a swab of oral or nasal mucosa, or a swab of skin or clothing.

18. The method of claim 16, wherein each of the plurality of diagnostic test cartridges comprises a sample chamber to receive the sample, a reagent chamber for storing the at least one diagnostic test reagent, and a reaction chamber for conducting the diagnostic testing, wherein the sample chamber, the reagent chamber, and the reaction chamber are in selective fluidic communication with each other.

19. The method of claim 16, wherein the diagnostic testing instrument does not remove any substance from the plurality of diagnostic test cartridges.

20. The method of claim 16, wherein the diagnostic testing comprises detection of a nucleic acid or a protein.

21. The method of claim 16, wherein the diagnostic testing comprises an amplification reaction of a nucleic acid.

22. The method of claim 21, wherein the amplification reaction is a polymerase chain reaction (PCR).

23. The method of claim 22, wherein the PCR is a real-time PCR.

24. The method of claim 16, wherein the passenger information apparatus further sends the test result to a mobile device belonging to the passenger.

25. The method of claim 16, wherein the first database is updated every 24 hours.

26. The method of claim 16, wherein the passengers' travel itinerary comprises all geographic locations the passengers traveled to within the previous 20 days.

27. The method of claim 16, further comprising placing the passenger in isolation when the diagnostic testing result indicates the presence of the pathogen or pathogens in the sample.

28. The method of claim 16, wherein the pathogen is the Ebola virus.

29. The method of claim 16, wherein the alert signal is also sent to a passenger's mobile communication device.

30. The method of claim 16, further comprising automated conveyance of the plurality of diagnostic test cartridges to the diagnostic testing instrument.

* * * * *